United States Patent [19]

Mathias et al.

[11] Patent Number: 4,793,949

[45] Date of Patent: Dec. 27, 1988

[54] NEW VINYL MONOMERS CAPABLE OF FORMING SIDE-CHAIN LIQUID CRYSTALLINE POLYMERS AND THE RESULTING POLYMERS

[75] Inventors: Lon J. Mathias; Robert E. Hermes, both of Hattiesburg, Miss.

[73] Assignee: University of Southern Mississippi, Hattiesburg, Miss.

[21] Appl. No.: 869,991

[22] Filed: Jun. 3, 1986

Related U.S. Application Data

[62] Division of Ser. No. 787,051, Oct. 15, 1985, Pat. No. 4,163,656.

[51] Int. Cl.$^4$ ............................................... G09F 5/00
[52] U.S. Cl. ..................................... 260/404; 560/41; 560/145; 560/172; 562/449; 562/450; 562/574
[58] Field of Search ................ 260/404; 562/574, 449, 562/450; 560/172, 145, 41

[56] References Cited

U.S. PATENT DOCUMENTS 2,622,074  12/1952  Coover, Jr. et al. .............. 260/77.5
4,634,775   1/1987  Beck et al. ........................ 548/402

FOREIGN PATENT DOCUMENTS 2201478  8/1972  European Pat. Off. .
0107815  5/1984  European Pat. Off. .
0113330  7/1984  European Pat. Off. .

OTHER PUBLICATIONS

Gallina et al., Synthesis of 2-Alkoxy-2-Acylaminopropionic Acids by Alkoxymercuration-Demercuration of 2-Acylaminoacrylic Acids, Journal of the Chemical Society, Perkin Transactions I, Organic and Bio-Organic Chemistry, vol. 10, pp. 1134–1136, (1973).

*Primary Examiner*—Charles F. Warren
*Assistant Examiner*—Elizabeth A. Hanley
*Attorney, Agent, or Firm*—Wegner & Bretschneider

[57] ABSTRACT

There is disclosed a new vinyl monomer capable of forming polymeric vesicles, micelles, monolayers, and side-chain liquid crystalline polymers. The vinyl monomer is of the formula

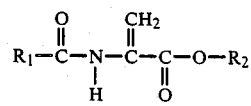

wherein $R_1$ is substituted or unsubstituted long chain alkyl or aryl and $R_2$ is a hydrogen atom, alkyl, or aryl.

The side-chain liquid crystalline polymers can be formed by free radical polymerization or by anionic polymerizations techniques. The different reaction methods give polymers of different configuration; the anionic technique results in a polymer having a nitrogen atom in the backbone. The polymers are useful in film and fiber formation and display good toughness.

4 Claims, 3 Drawing Sheets

NEW VINYL MONOMERS CAPABLE OF FORMING SIDE-CHAIN LIQUID CRYSTALLINE POLYMERS AND THE RESULTING POLYMERS

This application is a divisional of Ser. No. 787,051, filed Oct. 15, 1985, now U.S. Pat. No. 4,163,656 issued Sept. 23, 1986.

BACKGROUND OF THE INVENTION

The present invention is directed to new vinyl monomers capable of forming side-chain liquid crystalline polymers and the polymers resulting therefrom. More particularly, the invention is directed to vinyl monomers (alpha-aminopropenoic acid derivatives) of the formula

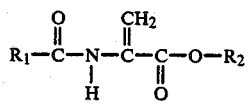

wherein $R_1$ is a substituted or unsubstituted long-chain alkyl or aryl group and $R_2$ is a hydrogen atom, alkyl, or aryl group. Polymers made from the new monomers possess side-chain liquid crystalline groups and the polymers can be formed by either free radical polymerization or by anionic polymerization techniques.

DESCRIPTION OF THE PRIOR ART

The preparation of alpha-aminopropenoic acid derivatives having low molecular weight substituents attached to the carbonyl group are known; see for example U.K. patent specification No. 1,354,571. These compounds are useful as biochemical antibiotic precursors, synthetic nucleic acid mimics, and cross-linking agents. To date, no compounds have been formed wherein long-chain alkyl groups, i.e., those with 5 to 17 carbon atoms in the chain, are present in the locations of $R_1$ and $R_2$ in the foregoing formula.

GENERAL DESCRIPTION OF THE INVENTION

The present invention is directed to alpha-aminopropenoic acid derivatives of the formula

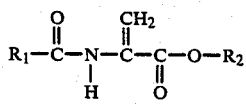

wherein $R_1$ is substituted or unsubstituted long-chain alkyl or aryl and $R_2$ is a hydrogen atom, alkyl, or aryl group. Because of the amphiphilic nature of these new monomers, they are capable of forming very stable vesicles, micelles, and monolayers that may be polymerized to give stable encapsulated solutions.

One method for the production of the alpha-aminopropenoic acid derivatives of the present invention is a multi-step procedure starting from commercially available D,L-serine wherein the serine is treated to form the hydrochloride salt (optionally esterified) which is then reacted with an acid chloride

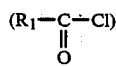

to form a serine derivative of the formula

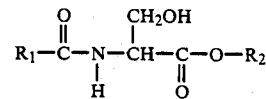

which in turn is reacted to convert the serine to an alanine derivative comparative of the formula of the alpha-aminopropenoic acid derivatives of the present invention.

Another method for the production of the alpha-aminopropenoic acid derivatives of the present invention is a multi-step procedure starting from commercially available D,L-serine wherein the serine is treated to form the hydrochloride salt (optionally esterified) which is then reacted with phosphorous pentachloride ($PCl_5$) and an acid chloride to form an alanine derivative of the formula

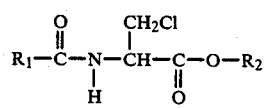

which in turn is reacted to convert the beta-chloroalanine to an alanine derivative comparable to the formula of the alpha-aminopropenoic acid derivatives of the present invention.

Polymers can be made from the monomer using either normal free radical conditions or an anionic procedure that is described in more detail infra.

The polymers made with the alpha-aminopropenoic acid derivatives of the present invention have biocompatible and/or biodegradable uses such as (i) encapsulation for controlled drug release, (ii) functional vesicles for antibody or antigen specific diagnostic tests, (iii) in vivo/in vitro studies of the mechanism(s) of endocytosis, (iv) impact modifiers of commercial polymers, i.e., a polymeric plasticizer, and (v) monolayer and Langmuir/Blodgett film-formers which can be subsequently polymerized and used for surface modification and coatings applications.

DETAILED DESCRIPTION OF THE INVENTION

Figure 1:
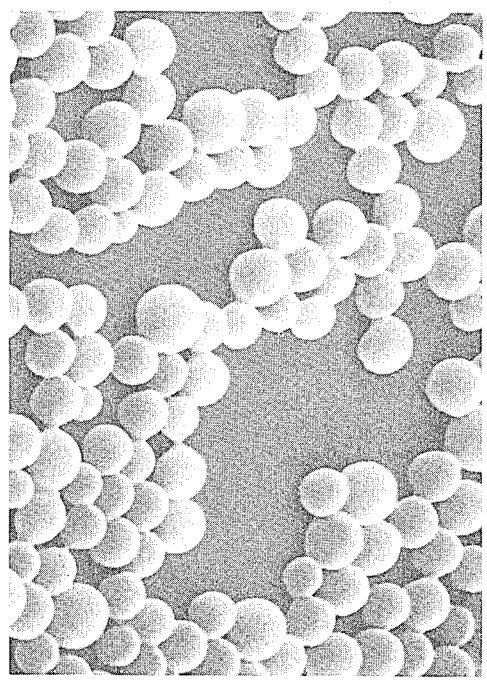
FIG. 1 is an S.E.M. photograph of vesicles formed by the polymerized monomers of the present invention and is discussed at Examples 4, infra.

Alpha-aminopropenoic acid derivatives of the present invention are characterized by the presence of a long-chain alkyl group, either substituted or unsubstituted, adjacent the amide-carbonyl moiety. Representative $R_1$ groups include $C_5$ to $C_{20}$ alkanes, both straight and branched chain, perfluoroalkyl, phenyl, halophenyl, and lower alkyl phenyl groups. Among the alkane groups, it is preferred to use $C_9$ to $C_{17}$ alkanes. Specific representative groups are $C_5H_{11}$, $C_9H_{19}$, $C_{13}H_{27}$, and $C_{17}H_{35}$ groups.

Representative R$_2$ groups include hydrogen, C$_1$ to C$_{18}$ alkanes, and aryl groups. The alkanes and aryl groups are similar to those shown in the R$_1$ groups but also include lower alkyl groups such as methyl, ethyl, propyl, and butyl, either substituted or unsubstituted.

The new monomers where R$_1$ is C$_9$ to C$_{17}$ can form vesicles because of the presence of both a hydrophilic end group and a hydrophobic tail (amphiphilic) which results in surfactant-like properties.

The two methods used for the production of the alpha-aminopropenoic acid derivatives of the present invention are: (i) the methyl esterification of D,L-serine in HCl saturated methanol, with subsequent reaction with the appropriate acid chloride, followed by dehydration of the serine residue by a CuCl catalysed reaction with a carbodiimide and (ii) the methyl esterification of D,L-serine in HCl saturated methanol, with subsequent reaction with phosphorous pentachloride (PCl$_4$) followed by reaction with the appropriate acid chloride and beta-chloro elimination (dehydrochlorination) using triethylamine base. Other lower alcohols, e.g. C$^{2-5}$-alkanols, can be used besides methanol.

In addition to the methods disclosed supra for the production of the alpha-aminopropenoic acid derivatives of the present invention, other synthetic routes are available for the production thereof including the treatment of alanine and cysteine. Other techniques include beta-elimination reactions on (i) O-mesylate or O-tosylate derivatives of serine, (ii) sulfinium or sulfinyl derivatives of cysteine, (iii) cysteine reacted with silver carbonate, and (iv) N-chloro derivatives of alanine. Also available are (v) the Hofmann degradation of diaminopropionyl residues, (vi) the rhenium sulfide catalyzed reaction of anhydrides with methyl-2-azidopropionate, and (vii) direct dehydration of serine residues with triphenylphosphine and diethyl azodidcarboxylate.

The new monomers of the present invention can be polymerized using free radical techniques and it has been found that the resulting polymer has a structure as follows:

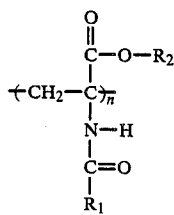

where n is an integer sufficient to give the resulting product a molecular weight of about 10,000 to about 14,000,000 as determined by capillary viscometry and Low Angle Laser Light Scattering [LALLS].

These polymers have been found to be soluble in a variety of organic solvents including acetone, chloroform, 1,4-dioxane, ethyl acetate, methylene chloride, and tetrahydrofuran.

The molecular weights of the polymers prepared to date by the free radical polymerization of the alpha-amino propenoic acid derivatives of the present invention range from 100,000 to 3,500,000 daltons, as determined by capillary viscometry and LALLS. Various peroxides and azo initiators can be used in the free radical polymerization. Representative compounds include potassium peroxydisulfate [K$_2$S$_2$O$_8$], 2,2'-azobis-(isobutyronitrile) [AIBN], and 2,2'-azobis-(2-amidinopropane)hydrochloride [V-50]. Photoinitiators such as V-50, 2,2-dimethoxy-2-phenyl acetophenone [Irgacure 651], diethoxy acetophenone [DEAP], and benzophenone can also be used.

It is also possible to form polymers from the alpha-aminopropenoic acid derivatives of the present invention by an anionic technique that results in a formation of polymers having the following formula:

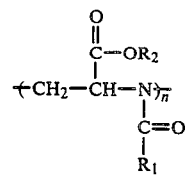

where n is an integer sufficient to give the resulting product a molecular weight of about 10,000 to about 1,500,000 as determined by capillary viscometry and LALLS.

It has been found that a polymer of this type is insoluble in common organic solvents except N,N-dimethylformamide and N,N-dimethylacetamide. The anionic polymerization technique which uses an alkyl lithium (or potassium alkoxide) initiator is similar to the method for preparing Nylon-3 from acrylamide. However, as can be seen from a review of the formula of the polymer, the carbonyl group is not within the backbone and depolymerization should not occur as readily as that for Nylon-3 type polymers. The polymers made by anionic polymerization techniques represent a new class of polymer containing a single nitrogen in the repeating unit with functional side groups and without the associated backbone carbonyl found in conventional polyamides.

The polymers of the present invention, including those prepared by free radical and anionic techniques, are new thermoplastic polymers having a high melting point and good toughness. The polymers can be used for both films and fiber formation.

Polymerization of the monomer by either of these techniques usually takes place for a period of seconds (anionic) to greater than four hours (free radical) at a temperature in the range from about room temperature to about 100° C., and at atmospheric pressure. It is preferred to undertake the polymerization for a period of up to 24 hours at temperatures between 60° C. to 100° C. (for both techniques) and at atmospheric pressure.

The following examples are representative of the invention.

EXAMPLE 1

The first method for monomer synthesis was accomplished by adapting published methods for the methyl esterification, N-acylation, and dehydration of D,L-serine to form N-alkanoyldehydroalanine methyl ester [methyl N-alkanoyl-alpha-aminopropenoate]. Commercial D,L-serine was reacted with excess HCl saturated methanol at 40° C. for 4 hours. After solvent removal under reduced pressure, and vacuum oven drying, the D,L-serine methyl ester hydrochloride salt was dissolved in a mixture of excess chloroform and two molar equivalents of triethylamine. While stirring constantly at 5° C., the appropriate acid chloride was added dropwise over a period of 4 hours. The clear solution so obtained was allowed to stir at 5° C. overnight to complete the reaction. The solution was extracted once with 0.1N HCl and again with an equal volume of pure water to remove the triethylamine hydrochloride salt. The chloroform phase was evaporated under reduced pressure to obtain a clear oil. In some cases, depending upon the length of $R_1$, the oil crystallized on standing at room temperature. The material so obtained was dissolved in excess methylene chloride to which was added 10% molar excess N,N-diisopropylcarbodiimide and 4% molar CuCl catalyst, and was held at 30° C. for at least 4 days or until the reaction was complete (as determined by caillary gas chromatography using a 25 meter SE-54 fused silica column with flame ionization detection). The suspension was filtered to remove the crystalline N,N-diisopropylurea side product. Solvent removal from the filtrate resulted in a green oil. Purification was accomplished by preparative column chromatography using a silica gel-methylene chloride system. Solvent removal resulted in a clear oil which was the N-alkanoyldehydroalanine methyl ester [methyl N-alkanoyl-alpha-aminopropenoate]. The advantage of this method is that the CuCl catalyst also inhibits spontaneous polymerization. A disadvantage of this method is the difficulty in purification for the removal of the copper salts formed in the reaction.

EXAMPLE 2

Using the method described described in Example 1, n-hexanoyl chloride [$C_6H_{11}OCl$] was used to obtain N-hexanoyldehydroalanine methyl ester [methyl N-hexanoyl-alphaaminopropenoate] as a clear yellow oil which was further purified by crystallization in isomeric hexanes at −40° C.

EXAMPLE 3

Using the method described in Example 1, n-decanoyl chloride [$C_{10}H_{19}OCl$] was used to obtain N-decanoyldehydroalanine methyl ester [methyl N-decanoyl-alpha-aminopropenoate] as a clear oil which was further purified by crystallization in isomeric hexanes at −40° C.

EXAMPLE 4

Using the method described in Example 1, n-myristoyl chloride [$C_{14}H_{27}OCl$] was used to obtain N-myristoyldehydroalanine methyl ester [methyl N-myristoyl-alpha-aminopropenoate] as an off-white mass which was further purified by crystallization in isomeric hexanes at −40° C.

EXAMPLE 5

Using the method described in Example 1, n-stearoyl chloride [$C_{18}H_{35}OCl$] was used to obtain N-stearoyldehydroalanine methyl ester [methyl N-stearoyl-alpha-aminopropenoate] as a white mass which was further purified by crystallization in isomeric hexanes at −15° C.

EXAMPLE 6

The second method for monomer synthesis was accomplished by adapting published methods for the methyl esterification, beta-chlorination, N-acylation, and dehydrochlorination of D,L-serine to form N-alkanoyldehydroalanine methyl ester [methyl N-alkanoyl-alpha-aminopropenoate]. Commercial D,L-serine was reacted with excess HCl saturated methanol at 40° C. for 4 hours. After solvent removal under reduced pressure, and vacuum oven drying, the D,L-serine methyl ester hydrochloride salt was added in small portions over a period of 2 hours to a stirred suspension of 10% molar excess phosphorous pentachloride in 2-nitropropane held at 10° C. The mixture was left at 10° C. overnight to complete the reaction. The suspension was filtered and the white crystalline product [3-chloroalanine methyl ester hydrochloride] was rinsed with methylene chloride and anhydrous acetone. The 3-chloroalanine methyl ester hydrochloride salt was added to excess benzene and stirred below 10° C. before adding a 1 molar equivalent of triethylamine base. Another molar equivalent of triethylamine base and 1 molar equivalent of the appropriate acid chloride were alternately added portionwise to a well stirred suspension over a period of 1 hour. A final equivalent of triethylamine base was added before the reaction mixture was brought to 40° C. for 2 hours to ensure complete reaction. Alternatively, the reaction mixture was placed in a refrigerator overnight. Capillary gas chromatography was used to determine if the reaction was complete [25M SE-54 fused silica column with flame ionization detection]. The suspension was filtered to remove the triethylamine hydrochloride salt and the filtrate was washed twice with 0.1N HCl and once with an equal volume of pure water. A pinch of hydroquinone was added to the organic phase to inhibit polymerization. Solvent removal under reduced pressure and moderate temperature resulted in a clear oil product which was the N-alkanoyldehydroalanine methyl ester [methyl N-alkanoyl-alpha-aminopropenoate]. This method affords a clean product which can be easily purified by repeated cold crystallizations from hexanes. The advantage of this method is the efficacy of the reaction(s) to obtain a pure product. The disadvantage is that the inhibitor has to be removed before polymerization can occur.

EXAMPLE 7

Using the method described in Example 6, n-hexanoyl chloride [$C_6H_{11}OCl$] was used to obtain N-hexanoyldehydroalanine methyl ester [methyl N-hexanoyl-alpha-aminopropenoate] as a yellow oil which was further purified by crystallization in isomeric hexanes at −40° C.

EXAMPLE 8

Using the method described in Example 6, n-heptanoyl chloride [$C_7H_{13}OCl$] was used to obtain N-heptanoyldehydroalanine methyl ester [methyl N-heptanoyl-alpha-aminopropenoate] as a yellow oil which was further purified by column chromatography using a silica gel/hexanes system. The purified material could not be crystallized.

EXAMPLE 9

Using the method described in Example 6, n-octanoyl chloride [$C_8H_{15}OCl$] was used to obtain N-octanoyldehydroalanine methyl ester [methyl N-octanoyl-alpha-aminopropenoate] as yellow oil which was further purified by crystallization in isomeric hexanes at −40° C.

EXAMPLE 10

Using the method described in Example 6, n-perfluorooctanoyl chloride [$C_8F_{15}OCl$] was used to obtain N-perfluorooctanoyldehydroalanine methyl ester [methyl N-perfluorooctanoyl-alpha-aminopropenoate] as a yellow oil which was further purified by crystallization in isomeric hexanes at −20° C.

EXAMPLE 11

Using the method described in Example 6, n-10-undecenoyl chloride [$C_{11}H_{19}OCl$] was used to obtain N-10-undecenoyldehydroalanine methyl ester [methyl N-10-undecenoyl-alpha-aminopropenoate] as a clear oil which was further purified by crystallization in isomeric hexanes at −40° C.

EXAMPLE 12

Using the method described in Example 6, n-decanoyl chloride [$C_{10}H_{19}OCl$] was used to obtain N-decanoyldehydroalanine methyl ester [methyl N-decanoyl-alpha-aminopropenoate] as a clear oil which was further purified by crystallization in isomeric hexanes at −40° C.

EXAMPLE 13

Using the method described in Example 6, n-lauroyl chloride [$C_{12}H_{23}OCl$] was used to obtain N-lauroyldehydroalanine methyl ester [methyl N-lauroyl-alpha-aminopropenoate] as a clear oil which was further purified by crystallization in isomeric hexanes at −20° C.

EXAMPLE 14

Using the method described in Example 6, n-stearoyl chloride [$C_{18}H_{35}OCl$] was used to obtain N-stearoyldehydroalanine methyl ester [methyl N-stearoyl-alpha-aminopropenoate] as a white mass which was further purified by crystallization in isomeric hexanes at −15° C.

EXAMPLE 15

Free radical polymerizations were performed in isomeric hexanes using AIBN initiation at 60° C. Approximately one gram of monomer was dissolved in an isomeric mixture of hexanes (dried over 4A molecular sieves) containing about 100 mg AIBN. Dry nitrogen was passed through the mixture contained in a septum-capped test tube for 5 minutes. The polymerization tube was then placed into a constant temperature oil bath maintained at 60° C. for at least 4 hours and up to 24 hours. Solvent removal resulted in a clear polymer which was dissolved in tetrahydrofuran and reprecipitated into ice cold methanol. The polymer was vacuum oven dried to remove traces of solvent.

EXAMPLE 16

Using the method described in Example 15, six polymerizations of N-decanoyldehydroalanine methyl ester were performed and the polymers were characterized by capillary viscometry and LALLS in tetrahydrofuran. The intrinsic viscosities ranged from 0.36 dl/g to 3.5 dl/g which correspond to weight average molecular weights [Mw] of 100,000 to 3,500,000. Polarized optical microscopy (using a controllable heated stage) revealed a softening point at 80° C. with birefringence occurring under slight application of pressure to the sample coverslip. The birefringence is characteristic of thermotropic liquid crystallinity displayed by side-chain comb-like polymers. The polymer was soluble in acetone, chloroform, ethyl acetate, 1,4-dioxane, 2-propanol methylene chloride, and tetrahydrofuran. The polymer only swelled in petroleum ether, methanol, ethanol, N,N-dimethyl acetamide, and N,N-dimethylformamide.

EXAMPLE 17

A 1.4 g sample of purified N-decanoyldehydroalanine methyl ester monomer was placed into a small screw cap vial. Within 3 days, under refrigerated conditions, the monomer had spontaneously polymerized into a clear solid. This is indicative of vinyl monomers which can autopolymerize by a free radical mechanism. The polymer was dissolved in tetrahydrofuran [THF], reprecipitated into ice cold methanol, and vacuum oven dried. The intrinsic viscosity in THF at 25° C. was 8.7 dl/g which corresponds to a weight average molecular weight [Mw] of 14,000,000 daltons, as determined by extrapolation from the Mark-Houwink plot of other data.

EXAMPLE 18

The anionic polymerization was performed in an isomeric mixture of hexanes using N-butyllithium or potassium tert-butoxide as the initiator. A clean, 120° C. oven-dried test tube was charged with about 1 gram of N-decanoyldehydroalanine methyl ester and 5.0 ml isomeric hexanes (dried over 4A molecular sieves). A pinch of N-phenyl-2-naphthylamine was added (to inhibit free radical polymerization) and the tube was capped with a serum stopper. Dry nitrogen was passed through the mixture for 5 minutes before placing in an oil bath held at 60° C. Initiation of the reaction at 60° C. was accomplished by using an aliquot of a commercial solution of n-butyllithium in n-hexane, or by adding crystals of potassium tert-butoxide. The hydrogen transfer polymerization resulted in a polymer that immediately precipitated from the reaction medium. The polymer was insoluble in the more common organic solvents except for N,N-dimethyl formamide (DMF) and N,N-dimethylacetamide (DMAC). The polymerization is similar to that of the anionic method used to prepare Nylon-3 from acrylamide; cf, V.R. Pai Verneker et al., Poly. Comm., 25(12), p. 363 (1984) and the references cited therein. However, since the carbonyl functional group is not within the backbone, depolymerization should not occur as readily as that for the Nylon-3 -type polymers. This is the first example of a new class of polymers that contain a single nitrogen in the repeat unit without the associated backbone carbonyl found in all polyamides. This polymer also has a reactive carboxylate moiety adjacent to the main chain, as well as another carbonyl connected to the backbone nitrogen.

Anionic solution polymerization occurred via a new hydrogen transfer mechanism to give a new class of polymers with backbone nitrogen (similar, but different from polyethyleneimines, which do not have dual functionality). One possible mechanism is as follows:

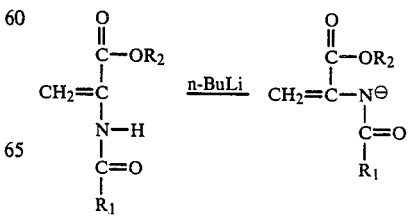

-continued

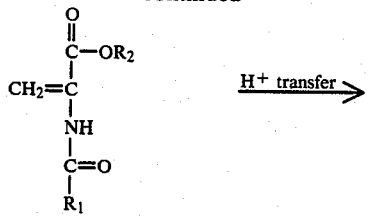

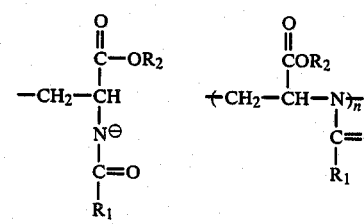

This polymer was soluble only in DMAC and DMF in contrast to the polymer obtained free radically which was soluble in many organic solvents. In addition, the polymer formed by anionic solution polymerization displayed lyotropic crystalline behavior in concentrated DMAC solutions. The liquid crystallinity observed under polarized optical microscopy is probably due to side-chain order.

Polarized optical microscopy of a concentrated solution of the anionically derived polymer in DMAC indicated lyotropic liquid crystallinity. Also, evidence for high crystallinity in a solution-drawn fiber indicates the possibility for processing from solutions.

EXAMPLE 19

The monomers of Examples 3 and 5 also, exhibited amphiphilic behavior in forming stable vesicles at 1–5% by weight in water after sonication. Radical polymerization of these vesicles gave stable spheres. Infrared spectroscopic analysis of the polymerized vesicles suggests a polymer configuration similar to that obtained by the normal free radical solution polymerization.

EXAMPLE 20

The formation of vesicles was accomplished by sonication of a 1 to 5% aqueous suspension of N-decanoyldehydroalanine methyl ester at room temperature for one hour. Stable vesicles were formed (liposomes) as observed by optical microscopy. A thermal, water-soluble initiator (potassium peroxydisulfate) was added to the aqueous suspension and resonicated for one-half hour. Polymerization was effected at 60° overnight to form spheres with an average diameter of 1.04 microns. For comparison, this is about 1/6 the size of normal human red blood cells (7.5 microns). A sample of the vesicles was melted on a microscope slide and the resulting polymer mass showed the same birefringent behavior as the polymer obtained from the free radical solution polymerization.

Figure 2:
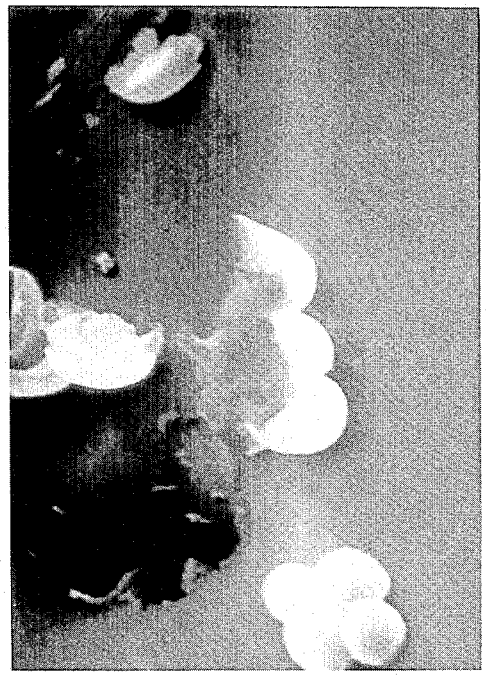
FIG. 2 is a photograph of the broken vesicles of FIG. 1.

A sample of the suspension was air-dried on a glass slide and coated with gold prior to scanning electron microscopy (SEM). The photograph depicted in FIG. 1 has a representative field at 8100X, showing almost perfect spheres with excess gold between them. The sample was then removed from the SEM chamber and gently scraped with a surgical knife blade. The photograph of FIG. 2 at 8100X shows broken spheres with distinct evidence of the hollow or "eggshell" structure.

EXAMPLE 21

The formation of vesicles was also accomplished by higher power sonication of a 1% suspension of N-stearoyldehydroalanine methyl ester in water for 30 seconds. Vesicles were formed with a greater distribution in size, and formation was recorded by light microscopy using videotape equipment.

EXAMPLE 22

Figure 3:
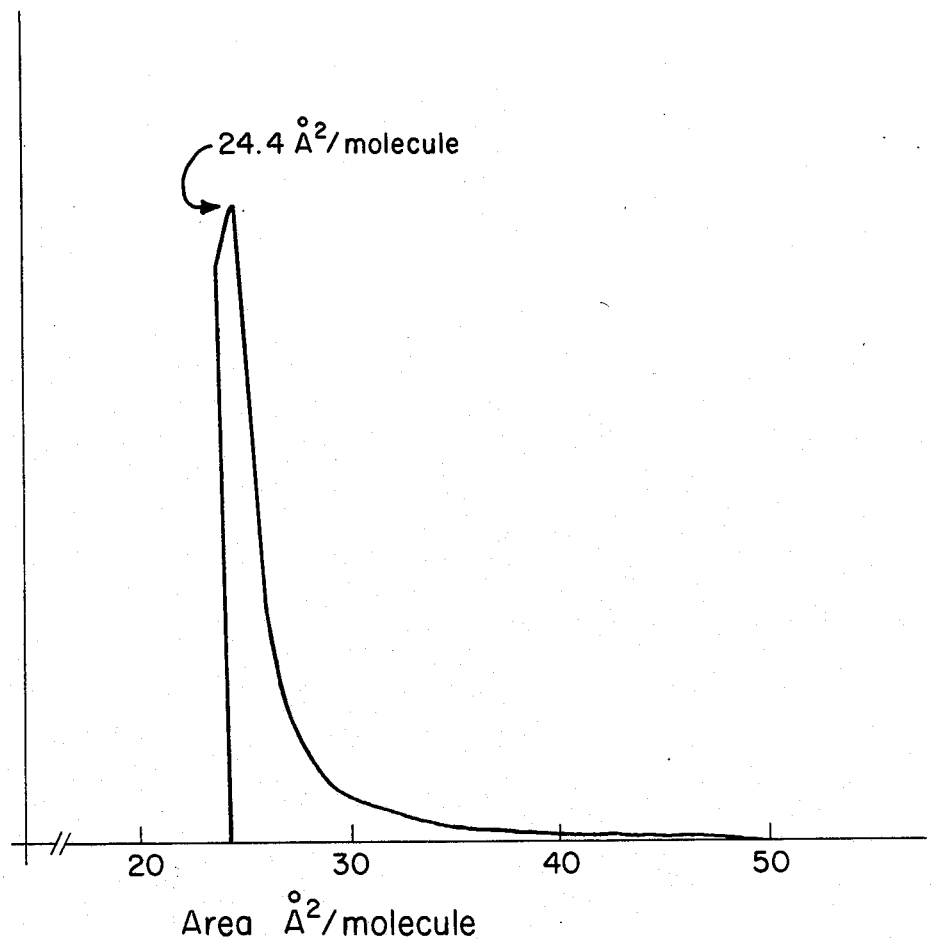
FIG. 3 is a pressure vs. area curve of the monolayer composed of N-stearoyldehydroalanine methyl ester at the air/water interface and is discussed at Example 22, infra.

The formation of a monolayer of material using N-stearoyldehydroalanine monomer was accomplished by depositing a known amount of material dissolved in n-hexane onto the surface of pure water contained within the boundaries of a Lauda-Brinkman Langmuir film balance. Upon evaporation of the n-hexane, the displacement of the moveable barrier was changed at a controlled rate to compress the monomer until collapse. FIG. 3 shows the pressure vs. area isotherm so obtained. The shape of the curve is typical of compounds which form stable monolayers at the air/water interface.

EXAMPLE 23

A monolayer of N-stearoyldehydroalanine methyl ester was polymerized by irradiating the monomer at the air/water interface with U.V. light (254 nm). A sample of monomer dissolved in n-hexane was deposited as described in Example 22. The barrier was moved in the compression mode until the surface pressure was 12 dynes/cm$^2$. The instrument maintained this pressure automatically throughout the experiment by changing the location of the barrier. Leaving the monolayer (without irradiation) for up to 1 hour did not reduce the area, which indicated the stability of the monomeric monolayer. Upon irradiation with U.V. light, an induction period was followed by a measureable decrease in the total area occupied by the monolayer. This implies that the monomer is changing from a condensed liquid/solid state to a more condensed polymeric state. Collection of the film and examination under cross polarization light microscopy revealed thermal behavior similar to a polymeric sample derived from free radical solution polymerization.

SUMMARY

In summary, these examples demonstrate the novel uses of these new monomers for the formation of:

1. new comblike polymers by radical polymerization;
2. new comblike polymers by anionic hydrogen transfer polymerization which forms a new class of functional polymers;
3. aqueous polymerization to form synthetic liposomes which could have use in the biomedical, biochemical, and organic chemical fields; and
4. monolayers that can be polymerized by U.V. light (without the aide of an initiator) to form a polymeric material which may have application in photoresists, molecular wave-guide supports, and surface modification.

The vesicles capable of being formed by the monomers of the present invention are believed to be filled with water although they may also be characterized as microemulsions.

What is claimed is:

1. A compound of the formula

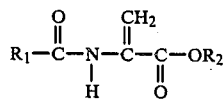
wherein $R_1$ is $C_9$ to $C_{17}$ alkyl and $R_2$ is selected from the group consisting of hydrogen, alkyl, and aryl.
2. The compound of claim 1 wherein $R_1$ is $C_9H_{19}$ and $R_2$ is $CH_3$.
3. The compound of claim 1 wherein $R_1$ is $C_{13}H_{27}$ and $R_2$ is $CH_3$.
4. The compound of claim 1 wherein $R_1$ is $C_{17}H_{35}$ and $R_2$ is $CH_3$.
* * * * *